United States Patent [19]
Grunewald

[11] Patent Number: 5,107,012
[45] Date of Patent: Apr. 21, 1992

[54] HYDROCYANATION OF PENTENENITRILES USING CYANOHYDRINS

[75] Inventor: Gerald C. Grunewald, Orange, Tex.
[73] Assignee: E. I. du Pont de Nemours and Company, Wilmington, Del.
[21] Appl. No.: 691,121
[22] Filed: Apr. 24, 1991
[51] Int. Cl.⁵ .......................................... C07C 253/30
[52] U.S. Cl. ..................................... 558/338; 558/335; 558/339
[58] Field of Search ..................... 558/335, 338, 339

[56] References Cited
U.S. PATENT DOCUMENTS
3,655,723  4/1972  Drinkard, Jr. ................. 558/335 X

*Primary Examiner*—Joseph Paul Brust

[57] ABSTRACT

Hydrocyanation of penetenenitriles using cyanohydrins as the HCN source and in which a solid dissociation additive is present in a slurry to facilitate the dissociation of the cyanohydrin.

6 Claims, 1 Drawing Sheet

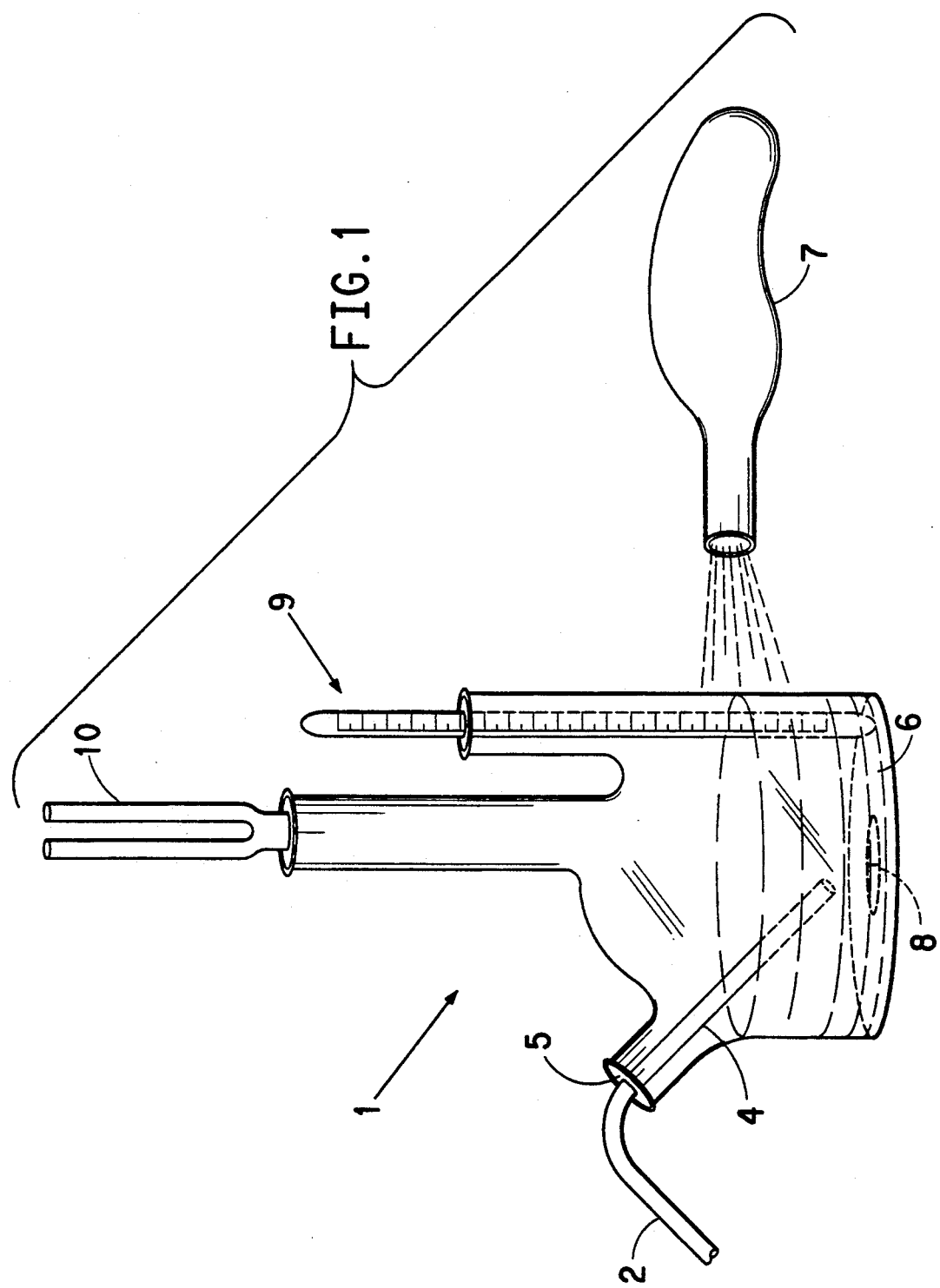

HYDROCYANATION OF PENTENENITRILES USING CYANOHYDRINS

FIELD OF THE INVENTION

This invention relates to the hydrocyanation of pentenenitriles using a cyanohydrin as the source of hydrogen cyanide.

BACKGROUND OF THE INVENTION

The hydrocyanation of olefins, including pentenenitriles, using cyanohydrin as the source of hydrogen cyanide is disclosed in Drinkard U.S Pat. No. 3,655,723. This Drinkard patent further discloses using as the catalyst for the reaction a mixture of a complex of a nickel and a sigma-pi bonding neutral ligand, an excess of said neutral ligand and a promoter for the catalyst. In this Drinkard patent the examples using pentenenitrile gave a product percent that is unattractive from a commercial point of view— the highest product percent for adiponitrile is 15.47 in example 22.

Commercial processes for the hydrocyanation of pentenenitriles employ hydrogen cyanide rather than cyanohydrins. Hydrogen cyanide at room temperature and atmospheric pressure is a gas that is very toxic, and great care must be taken in handling and shipping it. In fact some hydrocyanation plants manufacture hydrogen cyanide on-site so as to avoid the problems associated with shipping it.

Cyanohydrins are liquid or solid at room temperature and atmospheric pressure, and therefore far easier and safer to handle and ship.

It is an object of the present invention to provide a commercially attractive process for the hydrocyanation of pentenenitriles using cyanohydrins.

SUMMARY OF THE INVENTION

It has been discovered that a cyanohydrin can be effectively employed as the source of hydrogen cyanide in the hydrocyanation of pentenenitrile if an amount of solid high surface area dissociation additive is present in the reaction mixture and the mixture is agitated sufficiently to form a slurry.

More specifically this invention is a process for the hydrocyanation of pentenenitrile which comprises reacting at a temperature in the range of 35 to 65 degrees C., pentenenitrile, a cyanohydrin, a catalyst mixture of a complex of nickel and a sigma-pi bonding neutral ligand and an excess of said neutral ligand, a promoter for the catalyst, and a solid dissociation additive having a surface area in the range of 20 to 500 square meters per gram in an amount sufficient to effectively facilitate the dissociation of the cyanohydrin but said amount being not more than about 20% by weight of the total weight of a reaction mixture, while agitating the reaction mixture sufficiently to form a slurry of the solid dissociation additive in the otherwise homogeneous liquid phase reaction mixture.

DESCRIPTION OF THE DRAWING

The drawing is a representation of apparatus suitable to carry out the process of the invention in a semibatch manner.

DETAILED DESCRIPTION

Catalyst mixtures of a complex of nickel suitable for use in the process of the present invention are fully described in Drinkard et al's U.S. Pat. No. 3,496,215. The complexes have the general formula $Ni(PXYZ)_4$, wherein X is OR and Y and Z are selected from the class consisting of OR and R, wherein R is selected from the class consisting of alkyl and aryl groups having up to 18 carbon atoms, wherein the R radicals of a given ligand are so chosen that the ligand has a cone angle of 130° C. to 170° C. Specific ligands of the type PXYZ having a cone angle of between 130° and 170° include tri-o-tolyl phosphite (141°), di-o-tolylphenyl phosphonite (142°), and tri-(2,5-xylyl)phosphite (144°). Other suitable phosphorus ligands include tri-(2,4-xylyl)phosphite, tri-(o-phenylphenyl)phosphite, diphenylphenyl phosphonite and phenyl diphenyl phosphinite. The cone angle is determined as described by C. A. Tolman, J. Am. Chem. Soc. 92, 2956 (1970). The aryl groups of PXYZ may be substituted with alkoxy or other groups provided the groups do not interefere with the catalyst function. Mixed phosphorus ligands can be used. A general summary of Ni catalyzed hydrocyanation is found in Tolman, et al. Adv. Cat. 33, 1–46 (1985).

The hydrocyanation reaction can be carried out with or without a solvent. The solvent should be a liquid at the reaction temperature and pressure and inert toward the unsaturated compound and the metal complex. Generally, such solvents are hydrocarbons such as benzene, toluene, or xylene, or nitriles such as acetonitrile, benzonitrile or adiponitrile.

The exact temperature used is dependent to a certain extent on the particular complex and the desired rate. Generally, temperatures of from −35° C. to 65° C. can be used. The reactions may be carried out at atmospheric pressure or at a pressure above or below atmospheric depending upon the particular reactants being employed.

The cyanohydrin to be used as the source of hydrogen cyanide can be derived from almost any aldehyde or ketone. Suitable cyanohydrins include acetone cyanohydrin, acetaldehyde cyanohydrin, formaldehyde cyanohydrin, butyraldehyde cyanohydrin, methyl ethyl ketone cyanohydrin, methyl isopropyl ketone cyanohydrin, methyl t-butyl ketone cyanohydrin, cyclobutanone cyanohydrin, cyclopentanone cyanohydrin, cyclohexanone cyanohydrin, benzaldehyde cyanohydrin, p-methoxybenzaldehyde cyanohydrin, o-methoxybenzaldehyde cyanohydrin, diethylketone cyanohydrin, methylbutylketone cyanohydrin, cyclododecanone cyanohydrin, propionaldehyde cyanohydrin, and furfuraldehyde cyanohydrin.

In carrying out the hydrocyanation reaction the reactor may be charged with all of the reactants. Thus, the reactor is charged with the catalyst or catalyst components, the pentenenitrile, the solvent, and the particular cyanohydrin to be employed. Alternately, and preferably, the cyanohydrin can be introduced into the reactor containing the other reactants or the cyanohydrin and the pentenenitrile may be fed together into the reaction medium. The molar ratio of pentenenitrile to catalyst generally is varied from about 10:1 to 2000:1 for a batch operation.

A promoter is used to activate the catalyst for the hydrocyanation reaction. The promoter generally is a boron compound or a cationic form of the metal selected from the class consisting of zinc, cadmium, beryllium, aluminum, gallium, indium, thallium, titanium, zirconium, hafnium, erbium, germanium, tin, vanadium, niobium, scandium, chromium, molybdenum, tungsten, manganese, rhenium, thorium, iron, and cobalt. Among these, the cations of zinc, cadmium, titanium, tin, chromium, iron and cobalt are preferred. Suitable promoters of this type are salts of the metals listed above and include aluminum chloride, zinc chloride, cadmium iodide, titanium trichloride, titanium tetrachloride, zinc acetate, ethyl aluminum dichloride, chromic chloride, stannous chloride, zinc iodide, nickel chloride, cerous chloride, cobaltous iodide, cadmium chloride, molybdenum dichloride, zirconium chloride, thorium chloride, ferrous chloride, and cobaltous chloride.

The boron compounds are borohydrides or organoboron compounds, of which the organoboron compounds of the structure $B(R')_3$ are preferred. The borohydrides are the alkaline metal borohydrides, such as sodium borohydride and potassium borohydride, and the quaternary ammonium borohydrides, particularly the tetra(lower alkyl)ammonium borohydrides and borohydrides of the formula $B_nH_{n+4}$ where n is an integer of from 2 to 10 and $B_nH_{n+6}$ where n is an integer of from 4 to 10. When the boron compounds have the structure $B(R')_3$, $R'$ is selected from the class consisting of H, aryl radicals of from 6 to 18 carbon atoms, lower alkyl radicals of from 1 to 7 carbon atoms, and lower alkyl radicals of from 1 to 7 carbon atoms substituted with a cyano radical. Generally, the case where $R'$ is phenyl, as in triphenylborane, or phenyl substituted with an electro-negative radical is preferred. Many useful promoters are Lewis acids.

An excess of ligand such as an aryl phosphite or an aryl phosphine over that required for the metal complex is employed. The molar ratio of the excess ligand to the metal complex is at least 2:1 and preferably at least 8:1.

The solid dissociation additive useful in this invention must not be soluble in the reaction mixture, and must have a surface area in the range of about 20 to 500 square meters per gram, preferably greater than 200 square meters per gram. Suitable agents include inorganic oxides such as aluminum oxide, silicon oxide, magnesium oxide, boron oxide, and aluminosilicates. Ion exchange resins are also believed satisfactory.

The solid dissociation additive should be present in the reaction mixture in an amount sufficient to effectively facilitate the dissociation of the cyanohydrin. Normally the amount will be between about 1.5% and 20% by weight of the reaction mixture. The optimum amount will vary with the particular additive, the reaction conditions and the other components in the mixture, but the optimum amount is often in the range of about 10 and 15% by weight of the mixture. For recovery of the hydrocyanation products, conventional techniques may be employed such as crystallization of the product from solution or distillation. For recovery of the solid dissociative additive, conventional techniques may be employed such as filtration. This material can be recycled back to the process once it has been washed to remove species such as degraded catalyst and promoter. The carbonyl compounds liberated from the cyanohydrin complex, e.g. acetone, have been found to work well for this cleaning process. Other common solvents such as alcohols and ethers also work well.

The nitriles formed by the present invention are useful as chemical intermediates. For example, adiponitrile is an intermediate used in the production of hexamethylenediamine which is used in the production of polyhexamethyleneadipamide, a commercial polyamide useful in forming fibers, films, and molded articles. Other nitriles can be converted to the corresponding acids and amines which are conventional commercial products.

EXAMPLE 1

Into a 30 ml semibatch hydrocyanation reactor 1 in the drawing were charged:
(a) 4.837 g of tetrakis(tri-tolyl phosphite) Nickel (O) catalyst, i.e. NiL4 where L stands for ligand (tritolyl phosphite).
(b) 0.635 g of additional ligand.
(c) 14.528 g of pentenenitriles (PN's). The mixture is a combination of isomers, but is over 98% 3 and 4 PN's.
(d) 0.239 g of triphenyl boron (promoter).
(e) 5.00 g of $Al_2O_3$ (gamma alumina, neutral).

This reactor charge was prepared in a dry $N_2$ box because the catalyst, ligand, and promoter are all air and water sensitive. The alumina was dried in vacuo at 100° C. prior to use. A magnetic stir bar 8 was also added to the reactor.

The reactor was removed from the dry box and is set up as shown in the FIGURE. The system is purged with $N_2$ for several minutes to remove any air that may have entered during the assembly.

A disposable syringe was filled with 8 ml of acetone cyanohydrin and was placed in the syringe pump. The long needle 4 on the syringe was then put through one of the septa ports 5 of the reactor and was placed into the reaction liquid 6.

The heating unit 7 was turned on and the reactor was heated to 50° C. as measured by thermometer 9. The magnetic stirrer 8 was also turned on and the reaction media was vigorously stirred.

The syringe pump was turned on and the acetone cyanohydrin was delivered at a rate of 0.8 ml/hr.

The system was maintained at this reaction temperature for 22 hrs. The apparatus was fitted with condenser 10 which returned distillate to the reactor. At this point the system was disassembled and the reactor was weighed so that the exact amount of acetone cyanohydrin delivered would be determined. (7.26 g).

The reactor contents were filtered and the filtrate was analyzed via gas chromatography. The results reveal that 32% of the 3 & 4 pentenenitriles was converted with a 96% dinitrile selectivity to adiponitrile -- the desired linear product. The molar yield of adiponitrile was 92%.

ADDITIONAL EXAMPLES

Using the equipment described in Example 1, the process was repeated using several different solid dissociation additives. All of these examples were run using the same catalyst, cyanohydrin, and promoter as example 1, and using 15.5% by weight of the dissociation additive, unless otherwise noted. The results are shown below.

| Dissociation Additive | Surface Area ($m^2/g$) | PN Conv. (%) | ADN Yield (%) | 2PN Yield (%) |
|---|---|---|---|---|
| none | — | 4.8 | 88.0 | 7.8 |
| gamma $Al_2O_3$ | 145 | 29.8 | 92.1 | 4.2 |
| gamma $Al_2O_3$ | 200 | 31.8 | 92.2 | 4.0 |
| alpha $Al_2O_3$ | 0.04 | 4.1 | 88.1 | 7.7 |
| $SiO_2$ | 320 | 4.9 | 86.8 | 9.5 |
| Alumino-silicate | 425 | 11.3 | 90.1 | 5.4 |
| MgO | 120 | 6.9 | 88.0 | 7.6 |
| $B_2O_3$ | <100 | 7.0 | 88.5 | 7.3 |

I claim:

1. A process for the hydrocyanation of pentenenitrile which comprises reacting at a temperature in the range of 35 to 65 degrees C., pentenenitrile, a cyanohydrin, a catalyst mixture of a complex of nickel and a sigma-pi bonding neutral ligand and an excess of said neutral ligand, a promoter for the catalyst, and a solid dissociation additive having a surface area in the range of 20 to 500 square meters per gram in an amount sufficient to effectively facilitate the dissociation of the cyanohydrin but said amount being not more than about 20% by weight of the total weight of a reaction mixture, while agitating the reaction mixture sufficiently to form a slurry of the solid dissociation additive in the otherwise homogeneous liquid phase reaction mixture.

2. The process of claim 1 in which the solid dissociation additive is an inorganic oxide.

3. The process of claim 2 in which the inorganic oxide is selected from the class consisting of aluminum oxide, silicon oxide, magnesium oxide, boron oxide, and aluminosilicates.

4. The process of claim 1 in which the promoter is a Lewis acid.

5. The process of claim 4 in which the Lewis acid is selected from the class consisting of triphenyl boron, zinc chloride and triphenyl tin cyanide.

6. The process of claim 1 in which the cyanohydrin is selected from the class consisting of acetone cyanohydrin, acetaldehyde cyanohydrin, formaldehyde cyanohydrin, butyraldehyde cyanohydrin, methyl ethyl ketone cyanohydrin, methyl isopropyl ketone cyanohydrin, methyl t-butyl ketone cyanohydrin, cyclobutanone cyanohydrin, cyclopentanone cyanohydrin, cyclohexanone cyanohydrin, benzaldehyde cyanohydrin, p-methoxybenzaldehyde cyanohydrin, o-methoxybenzaldehyde cyanohydrin, diethylketone cyanohydrin, methylbutylketone cyanohydrin, cyclododecanone cyanohydrin, propionaldehyde cyanohydrin, and furfuraldehyde cyanohydrin.

* * * * *